United States Patent [19]

Cleary et al.

[11] 4,353,839

[45] Oct. 12, 1982

[54] PROCESS FOR SEPARATING SATURATED FATTY ACIDS

[75] Inventors: Michael T. Cleary, Elmhurst; Santi Kulprathipanja, Hoffman Estates, both of Ill.

[73] Assignee: UOP Inc., Des Plaines, Ill.

[21] Appl. No.: 238,231

[22] Filed: Feb. 25, 1981

[51] Int. Cl.$^3$ ............................................. C11C 1/08
[52] U.S. Cl. .................................. 260/419; 260/420; 260/428; 260/428.5
[58] Field of Search ............ 260/419, 420, 428, 428.5

[56] References Cited

U.S. PATENT DOCUMENTS

| | | | |
|---|---|---|---|
| 3,221,008 | 11/1965 | Wolf | 260/419 |
| 4,048,205 | 9/1977 | de Rosset | 260/428 |
| 4,049,688 | 9/1977 | de Rosset | 260/428 |
| 4,066,677 | 1/1978 | de Rosset | 260/428.5 |
| 4,125,550 | 11/1978 | Schoenenberger | 260/428 |
| 4,189,442 | 2/1980 | Lubsen | 260/428.5 |

*Primary Examiner*—John F. Niebling
*Attorney, Agent, or Firm*—James R. Hoatson, Jr.; Louis A. Morris; William H. Page, II

[57] ABSTRACT

A process for separating a one saturated fatty acid from a mixture of saturated fatty acids, which process comprises contacting the mixture at adsorption conditions with an adsorbent comprising a hydrophobic insoluble crosslinked polystyrene polymer, thereby selectively adsorbing the saturated fatty acid for which the adsorbent is selective. Preferably the adsorbed saturated fatty acid will be recovered from the adsorbent by desorption with a desorbent material.

10 Claims, 1 Drawing Figure

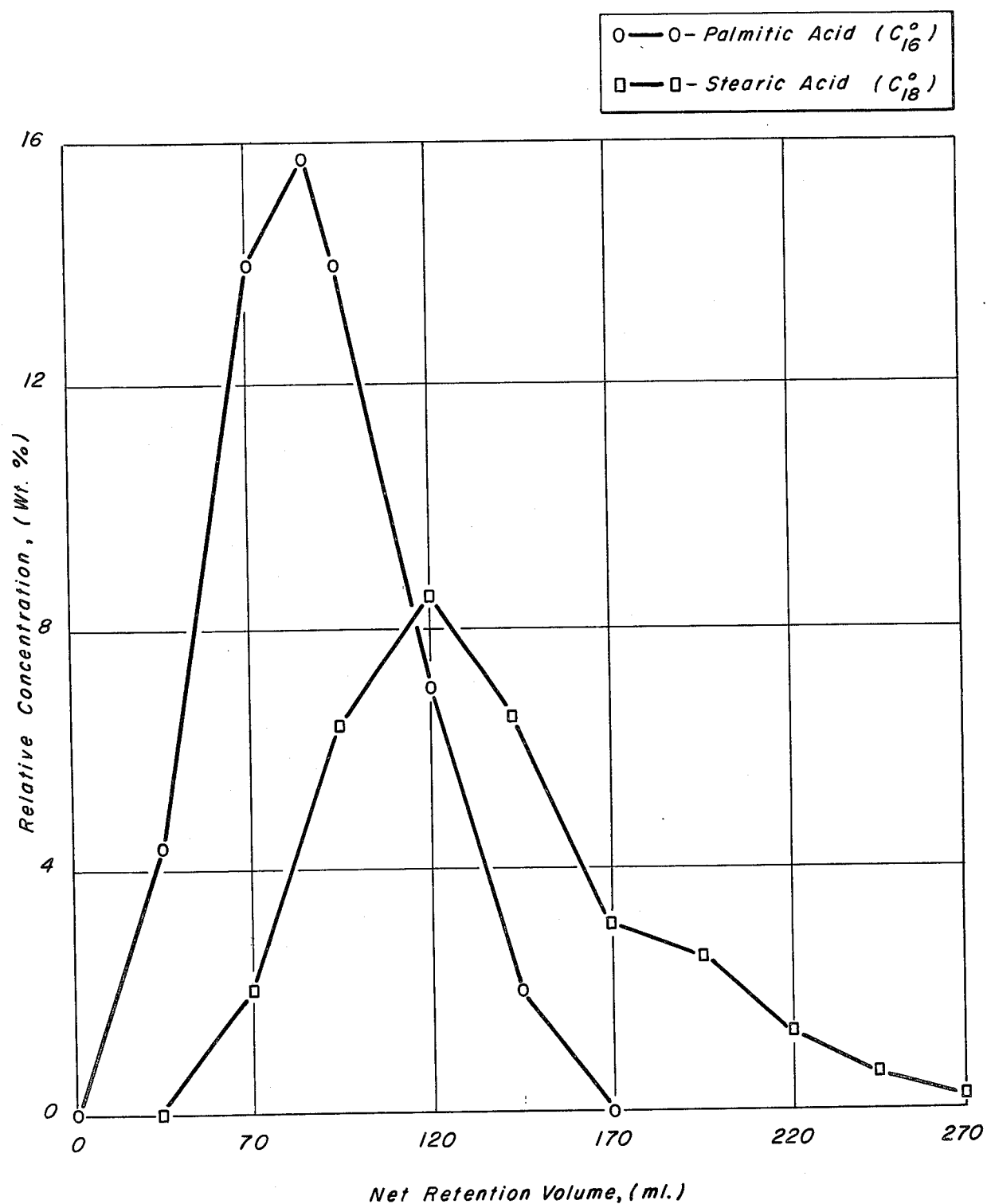

PROCESS FOR SEPARATING SATURATED FATTY ACIDS

BACKGROUND OF THE INVENTION

1. Field of the Invention

The field of art to which this invention pertains is the solid bed adsorptive separation of fatty acids. More specifically the invention relates to a process for separating saturated fatty acids which process employs an adsorbent comprising particular polymers which selectively adsorbs one fatty acid from a feed mixture containing more than one fatty acid.

2. Description of the Prior Art

It is known in the separation art that certain crystalline aluminosilicates can be used to separate certain esters of fatty acids from mixtures thereof. For example, in U.S. Pat. Nos. 4,048,205; 4,049,688 and 4,066,677 there are claimed processes for the separation of esters of fatty acids of various degrees of unsaturation from mixtures of esters of saturated and unsaturated fatty acids. These processes use adsorbents comprising an X or a Y zeolite containing a selected cation at the exchangeable cationic sites.

In contrast, this invention relates to the separation of certain fatty acids rather than fatty acid esters. We have discovered that adsorbents comprising hydrophobic insoluble crosslinked polystyrene polymers exhibit adsorptive selectivity for one saturated fatty acid with respect to another saturated fatty acid thereby making separation of such fatty acids by solid bed selective adsorption possible. In a specific embodiment our process is a process for separating stearic acid from palmitic acid. Substantial uses of fatty acids are in the plasticizer and surface active agent fields. Derivatives of fatty acids are of value of compounding lubricating oil, as a lubricant for the textile and molding trade, in special lacquers, as a waterproofing agent, in the cosmetic and pharmaceutical fields, and in biodegradable detergents.

SUMMARY OF THE INVENTION

In brief summary our invention is, in one embodiment, a process for separating a first saturated fatty acid from a mixture comprising the first saturated fatty acid and a second saturated fatty acid which process comprises contacting at adsorption conditions that mixture with an adsorbent comprising a hydrophobic insoluble crosslinked polystyrene polymer having adsorptive selectivity for the first saturated fatty acid, thereby selectively adsorbing the first saturated fatty acid.

In yet another embodiment our invention is a process for separating a first saturated fatty acid from a mixture comprising the first saturated fatty acid and a second saturated fatty acid which process employs an adsorbent comprising a hydrophobic insoluble cross-linked polystyrene polymer, which process comprises the steps of: (a) maintaining net fluid flow through a column of the adsorbent in a single direction, which column contains at least three zones having separate operational functions occurring therein and being serially interconnected with the terminal zones of said column connected to provide a continuous connection of the zones; (b) maintaining an adsorption zone in the column, the zone defined by the adsorbent located between a feed input stream at an upstream boundary of the zone and a raffinate output stream at a downstream boundary of the zone; (c) maintaining a purification zone immediately upstream from the adsorption zone, the purification zone defined by the adsorbent located between an extract output stream at an upstream boundary of the purification zone and the feed input stream at a downstream boundary of the purification zone; (d) maintaining a desorption zone immediately upstream from the purification zone, the desorption zone defined by the adsorbent located between a desorbent input stream at an upstream boundary of the zone and the extract output stream at a downstream boundary of the zone; (e) passing the feed mixture into the adsorption zone at adsorption conditions to effect the selective adsorption of the first saturated fatty acid by the adsorbent in the adsorption zone and withdrawing a raffinate output stream comprising the second saturated fatty acid from the adsorption zone; (f) passing a desorbent material into the desorption zone at desorption conditions to effect the displacement of the first saturated fatty acid from the adsorbent in the desorption zone; (g) withdrawing an extract output stream comprising the first saturated fatty acid and desorbent material from the desorption zone; (h) passing at least a portion of the extract output stream to a separation means and therein separating at separation conditions at least a portion of the desorbent material; and (i) periodically advancing through the column of adsorbent in a downstream direction with respect to fluid flow in the adsorption zone the feed input stream, raffinate output stream, desorbent input stream, and extract output stream to effect the shifting of zones through the adsorbent and the production of extract output and raffinate output streams.

Other embodiments of our invention encompass details about feed mixtures, adsorbents, desorbent materials and operating conditions all of which are hereinafter disclosed in the following discussion of each of the facets of the present invention.

DESCRIPTION OF THE INVENTION

At the outset the definitions of various terms used throughout the specification will be useful in making clear the operation, objects and advantages of our process.

A "feed mixture" is a mixture containing one or more extract components and one or more raffinate components to be separated by our process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. In this process a first fatty acid is an extract component and a second fatty acid is a raffinate component. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream and preferably at least a portion of the raffinate stream from the separation process are passed to separation means, typically fractionators, where at least a portion of desorbent material is separated to produce an extract product and a raffinate product. The terms "extract product" and "raffinate product" mean products produced by the process containing, respectively, an extract component and a raffinate component in higher concentrations than those found in the extract stream and the raffinate stream. Although it is possible by the process of this invention to produce a high purity, first or second fatty acid product (or both) at high recoveries, it will be appreciated that an extract component is never completely adsorbed by the adsorbent, nor is a raffinate component completely non-adsorbed by the adsorbent. Therefore, varying amounts of a raffinate component can appear in the extract stream and, likewise, varying amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of the first saturated fatty acid to that of the less selectively adsorbed second saturated fatty acid will be lowest in the raffinate stream, next highest in the feed mixture, and the highest in the extract stream. Likewise, the ratio of the concentration of the less selectively adsorbed second saturated fatty acid to that of the more selectively adsorbed first saturated fatty acid will be highest in the raffinate stream, next highest in the feed mixture, and the lowest in the extract stream.

The term "selective pore volume" of the adsorbent is defined as the volume of the adsorbent which selectively adsorbs an extract component from the feed mixture. The term "non-selective void volume" of the adsorbent is the volume of the adsorbent which does not selectively retain an extract component from the feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent. When adsorbent "passes" into an operational zone (hereinafter defined and described) employed in one embodiment of this process its non-selective void volume together with its selective pore volume carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in non-selective void volume of the adsorbent, it in most instances comprises less selectively retained feed components. The selective pore volume of an adsorbent can in certain instances adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

Before considering feed mixtures which can be charged to the process of our invention, brief reference is first made to the terminology and to the general production of fatty acids. The fatty acids are a large group of aliphatic monocarboxylic acids, many of which occur as glycerides (esters of glycerol) in natural fats and oils. Although the term "fatty acids" has been restricted by some to the saturated acids of the acetic acid series, both normal and branched chain, it is now generally used, and is so used herein, to include also related unsaturated acids, certain substituted acids, and even aliphatic acids containing alicyclic substituents. The naturally occurring fatty acids with a few exceptions are higher straight chain unsubstituted acids containing an even number of carbon atoms. The unsaturated fatty acids can be divided, on the basis of the number of double bonds in the hydrocarbon chain, into monoethanoid, diethanoid, triethanoid, etc. (or monoethylenic, etc.). Thus the term "unsaturated fatty acid" is a generic term for a fatty acid having at least one double bond, and the term "polyethanoid fatty acid" means a fatty acid having more than one double bond per molecule. Fatty acids are typically prepared from glyceride fats or oils by one of several "splitting" or hydrolytic processes. In all cases the hydrolysis reaction may be summarized as the reaction of a fat or oil with water to yield fatty acids plus glycerol. In modern fatty acid plants this process is carried out by continuous high pressure, high temperature hydrolysis of the fat. Starting materials most commonly used for the production of fatty acids include coconut oil, palm oil, inedible animal fats, and the commonly used vegetable oils, soybean oil, cottonseed oil and corn oil. The composition of the fatty acids obtained from the "splitter" is dependent on the fat or oil from which they were made. As detailed data for the fatty acid composition of fats have accumulated over a wide range of material, it has become more and more apparent that natural fats tend to align themselves, by their component acids, in groups according to their biological origin. Moreover, it has become clear that the fats of the simplest and most primitive organisms are usually made up from a very complex mixture of fatty acids whereas as biological development has proceeded, the chief component acids of the fats of the higher organisms have become fewer in number. In the animal kingdom this change in type is remarkably consistent and culminates, in the fats of the higher land animals, in fats in which oleic, palmitic and stearic acids are the only major components. All fats of aquatic origin contain a wide range of combined fatty acids, mainly of the unsaturated series. On passing from fats of aquatic to those of land animals there is also a marked simplification in the composition of the mixed fatty acids; most of the unsaturated acids, except oleic acid, disappear. The final result is that in most of the higher land animals the major component acids of the fats are restricted to oleic, palmitic and stearic and, moreover, that about 60–65% of the acids belong the the $C_{18}$ series, saturated or unsaturated. Thus the composition of the fatty acids obtained from the "splitter" can vary widely depending upon the fat or oil charged to the "splitter". Rarely will the composition of the fatty acid mixture obtained from the "splitter" be ideal or even satisfactory for most uses. Hence fractionation is used almost universally to prepare products more desirable for specific end uses than the mixtures obtained from the "splitter". Fractionation according to molecular weight is usually accomplished in fractional distillation. There is somewhat of a difference in the volatility of any two fatty acids of different chain length, and in practice, the utility of fractional distillation is enhanced by the absence of odd-membered acids in the natural fats, so that 2 carbon atoms is nearly always the minimum difference in chain length of the fatty acids present in a mixture. Fractionating columns in such operation are sometimes capable of producing fatty acids of 95% purity or better from the viewpoint of chain length depending on the chain length in question. It is not possible, however, to separate certain saturated fatty acids from each other by commercial fractional distillation, particularly stearic acid from palmitic acid which have carbon atom chain lengths of 18 and 16, respectively.

Our process is directed to separating certain mixtures of saturated fatty acids; more specifically it is directed to separating stearic acid from a mixture comprising stearic acid and palmitic acid. An example of a typical feed mixture is known as U.S. pharmaceutical grade "stearic acid", which in fact is about a 50—50 mixture of stearic and palmitic acids. Feed mixtures which can be charged to our process may contain, in addition to fatty acids, a diluent material that is not adsorbed by the adsorbent and which is preferably separable from the extract and raffinate output streams by fractional distillation. When a diluent is employed the concentration of diluent in the mixture of diluent and fatty acids may be from a few vol.% up to about 90 vol.%.

Desorbent materials used in various prior art adsorptive separation processes vary depending upon such factors as the type of operation employed. In the swing bed system in which the selectively adsorbed feed component is removed from the adsorbent by a purge stream, desorbent selection is not as critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Desorbent materials should additionally be substances which are easily separable from the feed mixture that is passed into the process. Both the raffinate stream and the extract stream are removed from the adsorbent in admixture with desorbent material and without a method of separating at least a portion of the desorbent material the purity of the extract product and the raffinate product would not be very high, nor would the desorbent material be available for reuse in the process. It is therefore contemplated that any desorbent material used in this process will preferably have a substantially different average boiling point than that of the feed mixture to allow separation of at least a portion of desorbent material from feed components in the extract and raffinate streams by simple fractional distillation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture. Finally, desorbent materials should also be materials which are readily available and therefore reasonable in cost. In the preferred isothermal, isobaric, liquid phase operation of the process of our invention, where the feed mixture comprises stearic and palmitic acids, we have found a mixture of dimethyl formamide and water to be a particularly effective desorbent material.

The prior art has also recognized that certain characteristics of adsorbents are highly desirable, if not absolutely necessary, to the successful operation of a selective adsorption process. Such characteristics are equally important to this process. Among such characteristics are: (1) adsorptive capacity for some volume of an extract component per volume of adsorbent; (2) the selective adsorption of an extract component with respect to a raffinate component and the desorbent material; and (3) sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions. Relative selectivity is shown as Equation 1 below:

Equation 1
$$\text{Selectivity} = (B) = \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1, it is preferred that such selectivity approach a value of 2. Like relative volatility, the higher the selectivity the easier the separation is to perform. Higher selectivities permit a smaller amount of adsorbent to be used. The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber comprising a helical column of approximately 70 cc volume having inlet and outlet portions at opposite ends of the chamber. The chamber is contained within a temperature control means and, in addition, pressure control equipment is used to operate the chamber at a constant pre-determined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a tracer and of a particular extract component or of a raffinate component or both all diluted in desorbent is injected for a duration of several minutes. Desorbent flow is resumed, and the tracer and the extract component or the raffinate component (or both) are eluted as in a liquid-solid chromatographic operation. The effluent can be analyzed onstream or alternatively effluent samples can be collected periodically and later analyzed separately by analytical equipment and traces of the envelopes of corresponding component peaks developed.

From information derived from the test adsorbent performance can be rated in terms of void volume, retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

To further evaluate promising adsorbent systems and to translate this type of data into a practical separation process requires actual testing of the best system in a continuous countercurrent liquid-solid contacting device. The general operating principles of such a device have been previously described and are found in Broughton U.S. Pat. No. 2,985,589. A specific laboratory size apparatus utilizing these principles is described in deRosset et al. U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and the raffinate and extract streams are being withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on the above-mentioned adsorbent testing apparatus and adsorbent evaluation techniques may be found in the paper "Separation of $C_8$ Aromatics by Adsorption" by A. J. deRosset, R. W.

Neuzil, D. J. Korous, and D. H. Rosback presented at the American Chemical Society, Los Angeles, Calif., Mar. 28 through Apr. 2, 1971.

Adsorbents to be used in the process of this invention will comprise hydrophobic insoluble crosslinked polystyrene polymers, preferably those manufactured by the Rohm and Haas Company and sold under the trade name "Amberlite". The type of Amberlite polymer known to be effective for use by this invention is referred to in Rohm and Haas Company literature as Amberlite XAD-2, and is described in the literature as "hard nonionic, insoluble spheres of high surface area, porous polymer". The various types of Amberlite polymeric adsorbents differ in physical properties such as porosity volume, surface area, average pore diameter, skeletal density and nominal mesh sizes. Applications for Amberlite polymeric adsorbents suggested in the Rohm and Haas Company literature include decolorizing pulp mill bleaching effluent, decolorizing dye wastes and pesticide removal from waste effluent. There is, of course, no hint in the literature to our surprising discovery of the effectiveness of Amberlite polymeric adsorbents in the separation of fatty acids.

A fundamental superiority of the Amberlite polymeric adsorbents over cyrstalline aluminosilicates is that the former, unlike the latter, may be used for the direct separation of fatty acids without first converting the fatty acids to their corresponding esters. The processes of the aforementioned prior art patents are applicable only to esters of fatty acids because the free carboxylic group of a fatty acid chemically reacts with the crystalline aluminosilicates used by those processes. The adsorbent of this invention exhibits no such reactivity and, therefore, the process of this invention is uniquely suitable for the separation of fatty acids.

The adsorbent may be employed in the form of a dense compact fixed bed which is alternatively contacted with the feed mixture and desorbent materials. In the simplest embodiment of the invention the adsorbent is employed in the form of a single static bed in which case the process in only semi-continuous. In another embodiment a set of two or more static beds may be employed in fixed bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Countercurrent moving bed or simulated moving bed countercurrent flow systems, however, have a much greater separation efficiency than fixed adsorbent bed systems and are therefore preferred. In the moving bed or simulated moving bed processes the adsorption and desorption operations are continuously taking place which allows both continuous production of an extract and a raffinate stream and the continual use of feed and desorbent streams. One preferred embodiment of this process utilizes what is known in the art as the simulated moving bed countercurrent flow system. The operating principles and sequence of such a flow system are described in U.S. Pat. No. 2,985,589 incorporated herein by reference thereto. In such a system it is the progressive movement of multiple liquid access points down an adsorbent chamber that simulates the upward movement of adsorbent contained in the chamber. Only four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divided the adsorbent chamber into separate zones, each of which has a different function. In this embodiment of our process it is generally necessary that three separate operational zones be present in order for the process to take place although in some instances an optional fourth zone may be used.

The adsorption zone, zone 1, is defined as the adsorbent located between the feed inlet stream and the raffinate outlet stream. In this zone, the feedstock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid absorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated to produce a desorbent stream which can be reused in the process and a raffinate product containing a reduced concentration of desorbent material. The separation means will typically be a fractionation column, the design and operation of which is well-known to the separation art.

Reference can be made to D. B. Broughton U.S. Pat. No. 2,985,589, and to a paper entitled "Continuous Adsorptive Processing—A New Separation Technique" by D. B. Broughton presented at the 34th Annual Meeting of the Society of Chemical Engineers at Tokyo, Japan on Apr. 2, 1969, both incorporated herein by reference, for further explanation of the simulated moving bed countercurrent process flow scheme.

Although both liquid and vapor phase operations can be used in many adsorptive separation processes, liquid-phase operation is preferred for this process because of the lower temperature requirements and because of the higher yields of extract product than can be obtained with liquid-phase operation over those obtained with vapor-phase operation. Adsorption conditions will include a temperature range of from about 20° C. to about 200° C. with about 20° C. to about 100° C. being more preferred and a pressure range of from about atmospheric to about 500 psig with from about atmospheric to about 250 psig being more preferred to insure liquid phase. Desorption conditions will include the same range of temperatures and pressures as used for adsorption conditions.

The size of the units which can utilize the process of this invention can vary anywhere from those of pilot plant scale (see for example our assignee's U.S. Pat. No. 3,706,812, incorporated herein by reference) to those of commercial scale and can range in flow rates from as little as a few cc an hour up to many thousands of gallons per hour.

The following example is presented to illustrate the selectivity relationship that makes the process of our invention possible. The example is not intended to unduly restrict the scope and spirit of claims attached hereto.

EXAMPLE

This example presents the results of using Amberlite XAD-2 for separating stearic acid from about a 50—50 mixture of stearic and palmitic acids diluted in desorbent in a ratio of desorbent to acid mixture of 90:10. The desorbent used was 85 wt. % dimethyl formamide and 15 wt. % water.

Data was obtained using the pulse test apparatus and procedure previously described at a temperature of 90° C. Specifically, the adsorbent was placed in a 70 cc helical coiled column and the following sequence of operations was used. Desorbent material was continuously run upflow through the column containing the adsorbent at a flow rate of 1.2 ml/min. At a convenient time the flow of desorbent material was stopped, and a 10 cc sample of feed mixture was injected into the column via a sample loop and the flow of desorbent material was resumed. Samples of the effluent were automatically collected in an automatic sample collector and later analyzed by chromatographic analysis.

FIG. 1 is a graphical presentation of the results of the pulse tests. FIG. 1 shows that stearic acid is more strongly adsorbed than palmitic acid, particularly for the desorbent mixture used. Furthermore, the separation achieved for this combination was substantial and clearly of commercial feasibility.

We claim as our invention:

1. A process for separating stearic acid from a mixture comprising said stearic acid and palmitic acid which comprises contacting said mixture at adsorption conditions with a nonionic hydrophobic insoluble crosslinked polystyrene polymer adsorbent in an adsorption column containing said adsorbent to selectively adsorb said stearic acid and to selectively permit the nonadsorbed portion of said mixture comprising palmitic acid to elute through said adsorption column.

2. The process of claim 1 further characterized in that said first saturated fatty acid is recovered by desorption with a desorbent at desorption conditions.

3. The process of claim 2 further characterized in that said adsorption and desorption conditions include a temperature within the range of from about 20° C. to about 200° C. and a pressure within the range of from about atmospheric to about 500 psig.

4. The process of claim 3 further characterized in that it is effected in the liquid phase.

5. The process of claim 1 further characterized in that said desorbent comprises dimethyl formamide and water.

6. A process for separating stearic acid from a mixture comprising said stearic acid and palmitic acid which process employs a nonionic hydrophobic insoluble crosslinked polystyrene polymer adsorbent, which process comprises the steps of:

(a) maintaining net fluid flow through a column of said adsorbent in a single direction, which column contains at least three zones having separate operational functions occurring therein and being serially interconnected with the terminal zones of said column connected so to provide a continuous connection of said zones;

(b) maintaining an adsorption zone in said column, said zone defined by the adsorbent located between a feed input stream at an upstream boundary of said zone and a raffinate output stream at a downstream boundary of said zone;

(c) maintaining a purification zone immediately upstream from said adsorption zone, said purification zone defined by the adsorbent located between an extract output stream at an upstream boundary of said purification zone and said feed input stream at a downstream boundary of said purification zone;

(d) maintaining a desorption zone immediately upstream from said purification zone, said desorption zone defined by the adsorbent located between a desorbent input stream at an upstream boundary of said zone and said extract output stream at a downstream boundary of said zone;

(e) passing said feed mixture into said adsorption zone at adsorption conditions to effect the selective adsorption of said stearic acid by said adsorbent in said adsorption zone and withdrawing a raffinate output stream comprising said palmitic acid from said adsorption zone;

(f) passing a desorbent material into said desorption zone at desorption conditions to effect the displacement of said stearic acid from the adsorbent in said desorption zone;

(g) withdrawing an extract output stream comprising said stearic acid and desorbent material from said desorption zone;

(h) passing at least a portion of said extract output stream to a separation means and therein separating at separation conditions at least a portion of said desorbent material from said stearic acid; and, (i) periodically advancing through said column of adsorbent in a downstream direction with respect to fluid flow in said adsorption zone the feed input stream, raffinate output stream, desorbent input stream, and extract output stream to effect the shifting of zones through said adsorbent and the production of extract output and raffinate output streams.

7. The process of claim 6 further characterized in that it includes the step of passing at least a portion of said raffinate output stream to a separation means and therein separating at separation conditions at least a portion of said desorbent material from said palmitic acid to produce a raffinate product having a reduced concentration of desorbent material.

8. The process of claim 6 further characterized in that it includes the step of maintaining a buffer zone immediately upstream from said desorption zone, said buffer zone defined as the adsorbent located between the desorbent input stream at a downstream boundary of said buffer zone and the raffinate output stream at an upstream boundary of said buffer zone.

9. The process of claim 6 further characterized in that said adsorption conditions and desorption conditions include a temperature within the range of from about 20° C. to about 200° C. and a pressure within the range of from about atmospheric to about 500 psig to insure liquid phase.

10. The process of claim 1 further characterized in that said desorbent comprises dimethyl formamide and water.

* * * * *